(12) United States Patent
Birlem

(10) Patent No.: US 7,333,202 B2
(45) Date of Patent: *Feb. 19, 2008

(54) YARN SENSOR

(75) Inventor: Olav Birlem, Schwalmtal (DE)

(73) Assignee: Oerlikon Textile GmbH & Co. KG, Monchengladbach (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/245,771

(22) Filed: Oct. 7, 2005

(65) Prior Publication Data

US 2006/0098201 A1    May 11, 2006

(30) Foreign Application Priority Data

Nov. 6, 2004 (DE) .................. 10 2004 053 736

(51) Int. Cl.
*G01N 21/84* (2006.01)
(52) U.S. Cl. ....................... 356/429; 356/430
(58) Field of Classification Search ........... 356/429, 356/430, 431
See application file for complete search history.

(56) References Cited

U.S. PATENT DOCUMENTS

| | | | |
|---|---|---|---|
| 3,907,440 A | 9/1975 | Eichenberger et al. | 356/199 |
| 4,739,176 A | 4/1988 | Allen et al. | 250/572 |
| 4,812,043 A * | 3/1989 | Vanstaen | 356/638 |
| 5,414,520 A | 5/1995 | Joss et al. | 356/430 |
| 5,499,794 A | 3/1996 | Aeppli | 250/559.45 |
| 5,768,938 A * | 6/1998 | Schilling et al. | 73/160 |
| 6,175,408 B1 | 1/2001 | Henze et al. | 356/238.3 |
| 6,380,548 B1 | 4/2002 | Henze et al. | 250/559.4 |
| 2001/0022656 A1 | 9/2001 | Henze et al. | 356/238.3 |

FOREIGN PATENT DOCUMENTS

| | | |
|---|---|---|
| CH | 643060 | 5/1984 |
| CH | 683293 A5 | 2/1994 |
| DE | 2337413 | 5/1974 |
| DE | 19859274 A1 | 6/2000 |
| DE | 199 39 711 A1 | 2/2001 |
| EP | 0 553 445 A2 | 8/1993 |
| EP | 0 572 592 B1 | 12/1993 |

(Continued)

OTHER PUBLICATIONS

German Search Report.

*Primary Examiner*—Roy M. Punnoose
(74) *Attorney, Agent, or Firm*—Kennedy Covington Lobdell & Hickman, LLP

(57) ABSTRACT

A yarn sensor for optically scanning a yarn (3), traveling longitudinally through a measurement gap (19), includes a light source (20) projecting a beam of light into the measurement gap (19), at least one receiver (23) for directly transmitted light, and light transmitting elements (24, 25, 26, 27) transmitting the light between the light source (20), measurement gap (19), and receivers (21, 22, 23). The light source (20) is an emitter with Lambert's emission characteristics. The light-transmitting element (27) includes a diaphragm and a lens, and the diaphragm is projected approximately into infinity. A diffusor (39) located between the light source (20) and the diaphragm generates radiation that passes through the diaphragm and is symmetrical to the optical axis of the lens. The yarn sensor can be used in the textile industry in spinning or bobbin winding machines with improved quality of the measurement results.

9 Claims, 4 Drawing Sheets

FOREIGN PATENT DOCUMENTS

| | | |
|---|---|---|
| EP | 0761585 A1 | 3/1997 |
| EP | 1 143 236 A2 | 10/2001 |
| EP | 1 508 798 A1 | 2/2005 |
| GB | 2064106 A | 6/1981 |
| WO | WO 93/19359 | 9/1993 |
| WO | WO 00/20849 | 4/2000 |
| WO | WO 2004/044579 A1 | 5/2004 |

* cited by examiner

YARN SENSOR

CROSS-REFERENCES TO RELATED APPLICATIONS

This application claims the benefit of German patent application 102004053736.4 filed Nov. 6, 2004, herein incorporated by reference.

BACKGROUND OF THE INVENTION

The present invention relates to a yarn sensor for optically scanning a yarn, moving in its longitudinal direction in a measurement gap.

Optical systems are often employed for contactless detection of yarn parameters with the yarn in motion in a spinning or bobbin winding machine. Optical systems are simple in their construction and function and can be made economically. They operate with shading or with reflected light. The test material is lighted by a light source.

European Patent Disclosure EP 0 761 585 A1 describes a generic type of yarn sensor with an optically functioning system that can likewise serve not only to determine the yarn diameter, but also to detect extraneous material in the yarn, such as extraneous fibers or contaminants. The surfaces in the measurement gap that are struck by light projected by the light source reflect this arriving light. The light reflected by the yarn, because of the small surface area of the yarn, represents a relatively small signal source. The yarn signal converted into current varies in the nanoampere range. Compared to the small irradiated surface of the yarn, the relatively large, dirty surface of the measurement gap, because of its length, represents a not inconsiderable source of reflection signals. The interfering radiation, which adulterates the result of the measurement, is also called a parasitic signal. Because of the low intensity of the yarn signal, a high amplification of the signal converted from the incident light at the yarn takes place, but high amplification of the parasitic signals occurs as well. This leads to an impermissibly small useful signal, in proportion to the total signal. The yarn sensor of European Patent Publication EP 761 585 A1 is incapable of overcoming this disadvantage.

Swiss Patent Disclosure CH 643 060, like European Patent Publication EP 0 761 585 A1, also describes an optical system for checking the yarn diameter. A measurement signal that is proportional to the diameter of the yarn is generated. Signal fluctuations that occur because of changes in the light intensity of the light source as a result of fluctuations in the supplied voltage, aging, or clouding are compensated with the aid of circuitry means. In an exemplary embodiment shown, a point light source emits a cone of light in the direction of a camera or other picture taker, and the yarn passing between the light source and the camera is projected as a shadow on the camera. A CCD line sensor serves as the camera. The extent of the shading on the camera is dependent on the diameter of the yarn. The location of the yarn and in particular the distance of the yarn from the camera has a marked influence on the size of the shaded area. For instance, if the yarn moves toward the camera while the yarn diameter remains constant, the shading becomes smaller, even though the yarn diameter has stayed the same. This leads to adulterations in the outcome of measurement.

In a further alternative exemplary embodiment shown in Swiss Patent Disclosure CH 643 060, an optical element is disposed between the light source, which is said to be of the point type, and the yarn and is intended to cast the light, emitted by the light source, onto the camera in the form of an approximately parallel beam. In this manner, it is intended that the shading and hence the outcome of measurement are no longer affected by the location of the yarn in the measurement region or measurement gap. Motions of the running yarn transversely to the running direction in the measurement region are tolerable in this case. The parallelism of the beam is dependent on whether the light source is ideally point-shaped. However, ideally point-shaped light sources are not available. Even with the incandescent bulbs that Swiss Patent Disclosure CH 643 060 describes and calls point light sources, the light is not generated at a point. Typically, in incandescent bulbs, the light is generated by a mounted incandescent filament. Since the precondition of a point-shaped light source cannot be met, neither the uniformly distributed luminous intensity nor the parallelism of the beam aimed at the camera can be attained, and remain inadequate. An outcome of measurement that is independent of the location of the yarn in the measurement gap is unattainable with the apparatus of Swiss Patent Disclosure CH 643 060.

Another possible way of purposefully generating parallel light is to convert the light emitted by a Lambert emitter. The light density of a Lambert emitter is constant in all directions of the half-space defined by the light-emitting face. That is, the Lambert emitter behaves like an ideal diffusely emitting face. Examples of widely used surface emitters of this kind are fluorescent lamps, but because of the required structural size, they are unsuitable for use in yarn measurement heads at the work stations of a spinning or bobbin winding machine. Light-emitting diodes are also area emitters, and as a rule have the attribute of having a Lambert conformal emission characteristic. By definition, the radiation emitted by every point in the surface of a Lambert emitter is embodied as a divergent beam of light.

German Patent Disclosures DE 23 37 413 B2 and DE 198 59 274 A1 show devices for monitoring a traveling yarn, in which light-emitting diodes are used as light sources, and photodiodes are used as light receivers.

SUMMARY OF THE INVENTION

It is accordingly an object of the present invention to improve the quality of the outcomes of measurement of a yarn sensor for optical scanning of a yarn traveling in its lengthwise direction through a measurement gap.

Briefly summarized, the present invention provides a yarn sensor for optically scanning a yarn traveling in its lengthwise direction through a measurement gap, basically comprising a light source for projecting a beam of light across the measurement gap, at least one receiver for directly transmitted light, and elements for transmitting the light between the light source, measurement gap and receivers. In accordance with the present invention, the light source comprises an emitter having an emission characteristic of a Lambert emitter. The light transmitting elements comprise a light transmitting element disposed between the light source and the measurement gap and including a diaphragm and a lens, downstream of the light source in the direction of light projection, and arranged such that the diaphragm is projected at least approximately into infinity. A diffusor is disposed between the light source and the diaphragm, the diffusor being adapted to shape the light beam passing through the diaphragm symmetrically to the optical axis of the lens.

The invention is based on the recognition that the light sources referred to as Lambert emitters, as used in a yarn cleaner, only inadequately exhibit behavior that approximates a Lambert emitter. This is due to engineering tolerances in production and inaccuracies in positioning upon assembly. These light sources operate with light-emitting diodes which project a beam of light that is not rotationally symmetrical to the optical axis of the system comprising the light source, the lens, and the receiver. The asymmetrical emission (sometimes referred to as "cross-eyed") varies from one light-emitting diode to the next.

Embodying the yarn sensor according to the present invention makes it possible for the scanned yarn in the measurement gap to move in a beam of light whose radiation is very homogeneous in its luminous intensity as well beams of light that extend parallel to one another and parallel to the optical axis. Thus when a yarn is detected by shading, substantially improved independence of the outcome of measurement on the location of the yarn in the measurement gap is achieved, compared to the prior art. Light loss, which is caused by scattered light and attenuates the measurement signals, is minimized.

The light source is advantageously a light-emitting diode. Light-emitting diodes require only little space and are therefore especially well suited to use at work stations of spinning or bobbin winding machines, where only very limited space is available.

The light-emitting diode is preferably embodied as a white-light LED. The color spectrum of the white-light LED offers a variety of possibilities in color recognition. The use of additional light-emitting diodes with light in other colors can be economically dispensed with, and the required space can be kept small. Since a white-light LED serving as the sole light source emits light in all the colors needed, a constant sensitivity of the yarn sensor to different colors is made possible. A single white-light LED comes substantially closer to the model of a point light source than an array of two or more light-emitting diodes.

Preferably, the diffusor is a film for generating a divergent beam of light having the characteristic of light emitted by a Lambert emitter. The lens of the first light transmitting element preferably comprises a light entrance side arranged to homogeneously distribute the luminous intensity the light beam from the light source in the direction of the optical axis of the lens and comprises an exit side arranged to project the light beam arriving from the entrance side essentially parallel to the optical axis of the lens. As the diffusor, a film of the type Oracal 8005, translucent series, made by the company known as and doing business as K. Gröner, may be used. This film has been used previously for advertising labels, that is, in a field that is completely different from use in a yarn sensor for increasing the measurement accuracy, as in the present invention. After passing through the lens, the bundle of light advantageously has a homogeneously distributed luminous intensity and a beam path that is quasi-parallel to the optical axis of the lens, and the entire beam has a divergence that tends toward zero. A point-shaped spot, for instance caused by a contaminant, does not lead to non-homogeneity of the beam in the measurement field, as long as the remaining light-emitting film emits light that meets the requirements for the Lambert conformal emission characteristic.

The yarn sensor may also preferably include second and third receivers for light reflected by the yarn for detecting extraneous fibers. The light-transmitting elements may comprise second and third light-transmitting elements respectively disposed between the measurement gap and the second and third reflected light receivers, each of the second and third light-transmitting elements comprising a lens disposed upstream in the projected direction of the light reflected from the yarn such that, in the absence of the yarn, projected images on an opposing surface of the measurement gap are detectable by the second and third receivers essentially outside both opposite sides of a projected image of the light source across the measurement gap.

With a yarn sensor of such construction, improved detection of extraneous substances in the yarn can be attained. Only light from the light source that is reflected by the yarn reaches the two receivers for reflected light. Interference and adulterations from so-called parasitic signals can be avoided. The measurement sensitivity of the yarn sensor can be adjusted more sensitively.

The diaphragm between the light source and the lens may advantageously have an aperture of a width between about 0.8 mm and about 1.2 mm. Such a diaphragm contributes to the fact that only light from the light source that is homogeneously distributed and is oriented parallel to the optical axis of the lens disposed upstream of the light source reaches the measurement gap. A second diaphragm with a rectangular aperture may also be disposed between the lens of the first light transmitting element and the yarn so as to define the beam of light aimed at the yarn in such a way that only surfaces that cause no reflections that lead to parasitic signals are illuminated.

With a yarn sensor according to the invention, the quality of the outcome of measurement in determining the yarn diameter and in detecting extraneous fibers is improved. By means of a light source and the optical transformation according to the invention, better homogeneity of the beam of light is attained. A broader measurement field is therefore possible, with simultaneous improvement to the homogeneity in the measurement field. As a result, a greater yarn motion in the measurement field can be tolerated, and it is optionally possible to dispense with yarn guides for guiding the yarn in the measurement gap. In this way, engineering effort and expense are saved, and the yarn suffers less damage. Soiling in the region of the yarn sensor from abrasion is reduced.

Further details, features and advantages of the present invention will be described and understood from following specification with reference to the illustrations in the accompanying drawings.

DESCRIPTION OF THE PREFERRED EMBODIMENT

Figure 1:
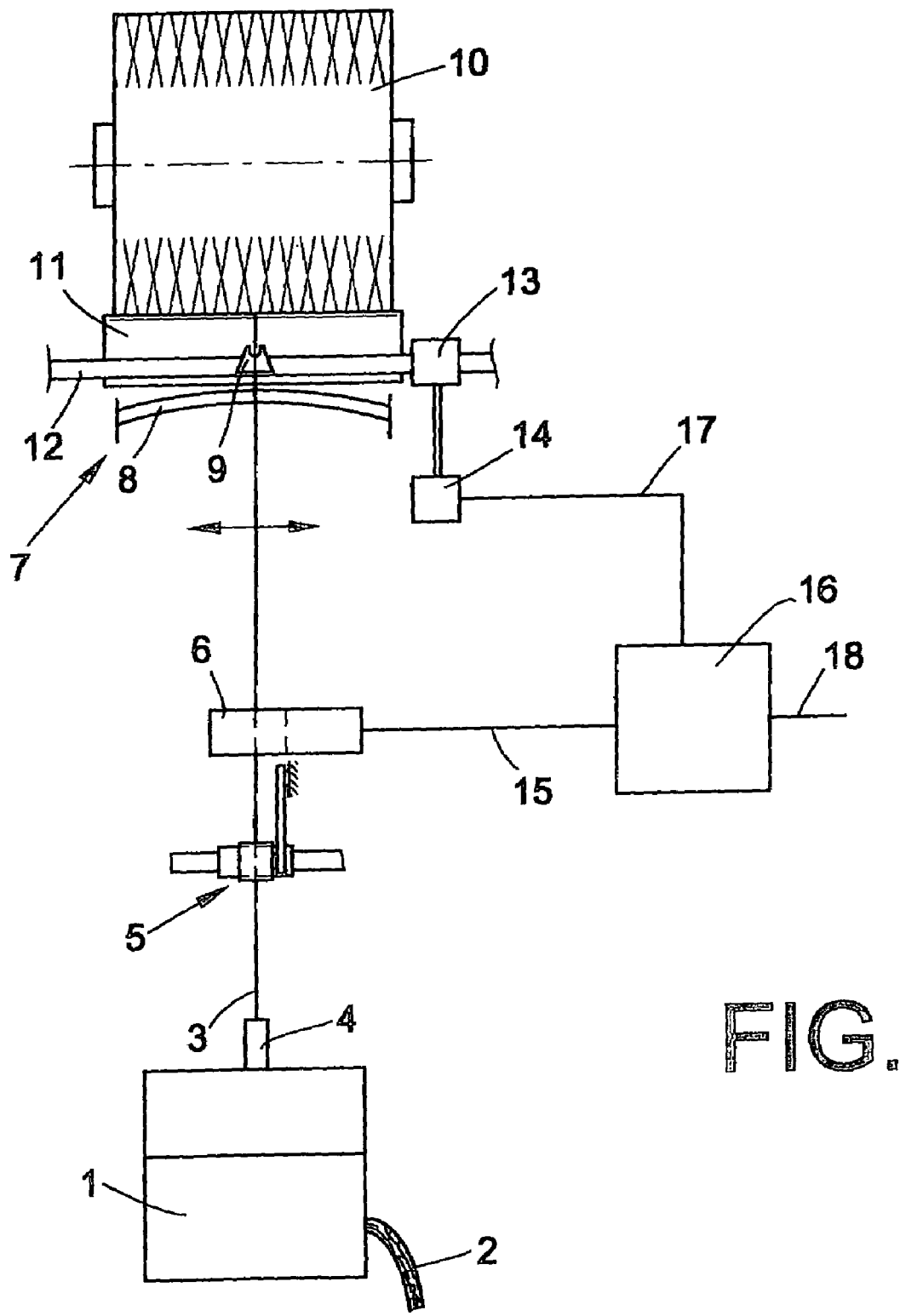
FIG. 1 is a schematic illustration of the basic elements of a yarn spinning station.

Referring now to the accompanying drawings, FIG. 1 shows a spinning box 1 of an open-end spinning machine, to which a sliver 2 is being delivered. The yarn 3 made in the spinning box 1 is withdrawn via the draw-off tube 4 by means of a pair of draw-off rollers 5, passes through a yarn sensor 6, and is directed via a hoop 8 to be wound up, by the reciprocating motion of a yarn guide 9 of a traversing device 7, over a predetermined width into a cross-wound bobbin, also referred to as a cheese 10. The cheese 10 is driven by means of a friction roller 11. The yarn guide 9 is secured to a yarn guide 12, which is moved back and forth by a yarn guide gear 13. The drive of the yarn guide gear 13 is effected by means of a drive device 14. The yarn sensor 6 for monitoring the moving yarn 3 is located above the pair of draw-off rollers 5, in the region of the traversing movement of the yarn 3. In an alternative embodiment, not shown, the yarn sensor 6 may be located upstream, instead of downstream, of the pair of draw-off rollers 5. The yarn sensor 6 communicates via a line 15 with a control unit 16, which receives the signals emitted by the yarn sensor 6. Via a further line 17, the control unit 16 is connected to the drive device 14. The drive device 14 is preferably embodied as an electric motor. Via the line 18, the control unit 16 communicates with further spinning stations, data processing devices, or spinning machines, not shown here.

Figure 2:
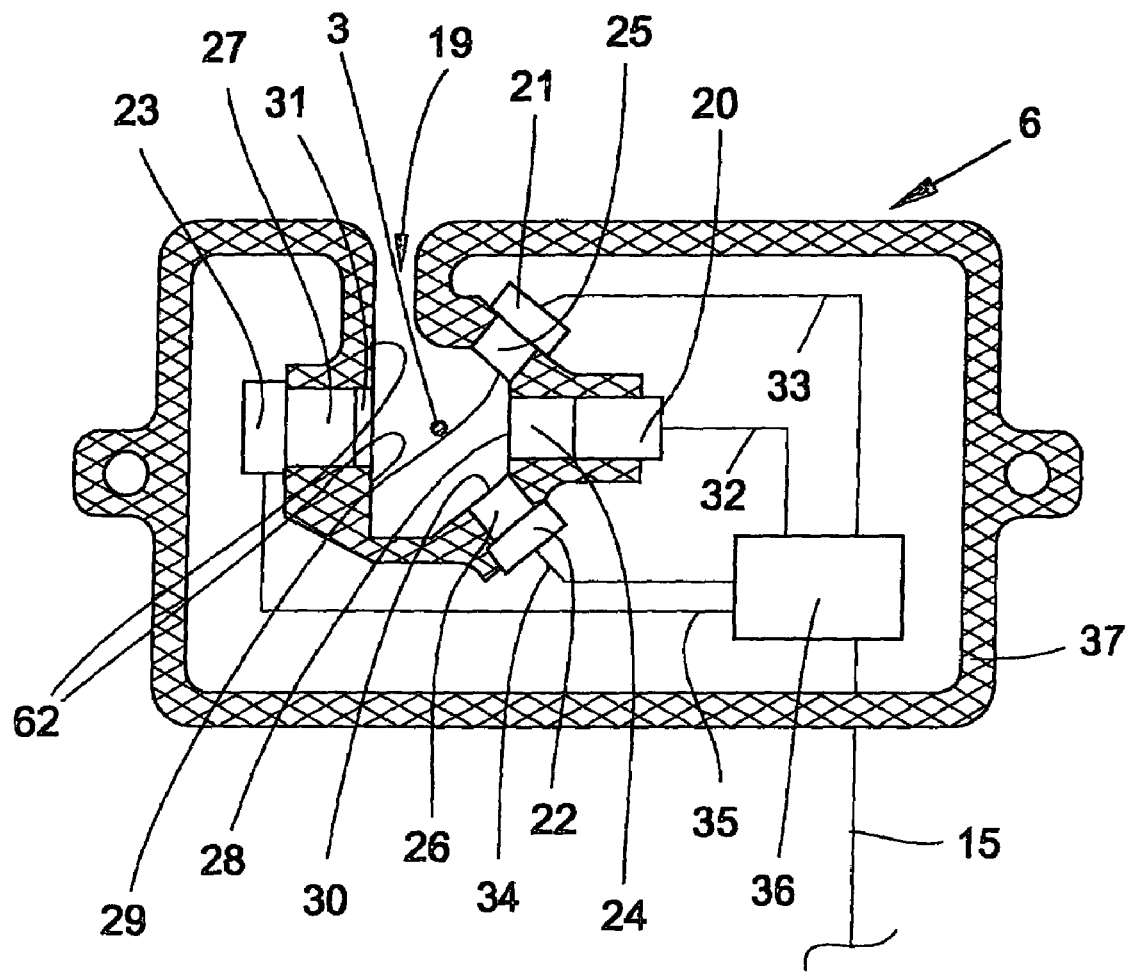
FIG. 2 is a cross-sectional view of a yarn sensor according to the present invention, showing the housing open.

From FIG. 2 depicts the location of individual components of the yarn sensor 6 relative to the measurement gap 19 and the yarn 3. The light source, embodied as a light-emitting diode 20, and photodiodes 21, 22, which serve to receive the light reflected by the yarn 3, are positioned to the right, as viewed in FIG. 2, of the measurement gap 19. A photodiode 23 for receiving the light transmitted directly by the light-emitting diode 20 is positioned to the left of the measurement gap 19, as viewed in FIG. 2. Elements 24, 25, 26, 27 for transmitting the light are disposed between the light-emitting diode 20 and the measurement gap 19, on the one hand, and between the measurement gap 19 and the photodiodes 21, 22, 23 on the other hand. The light transmitting elements 24, 25, 26, 27 are separated from the measurement gap 19 by windows 28, 29, 30, 31. The windows can provide protection of the light transmitting elements 24, 25, 26, 27 against becoming soiled with dust and fluff. The light-emitting diode 20 and the photodiodes 21, 22, 23 each communicate with a signal processing device 36 by means of the lines 32, 33, 34, 35. The signal processing device 36 communicates in turn with the control unit 16 via the line 15, which leads through the housing 37 of the yarn sensor 6 to the outside.

Figure 3:
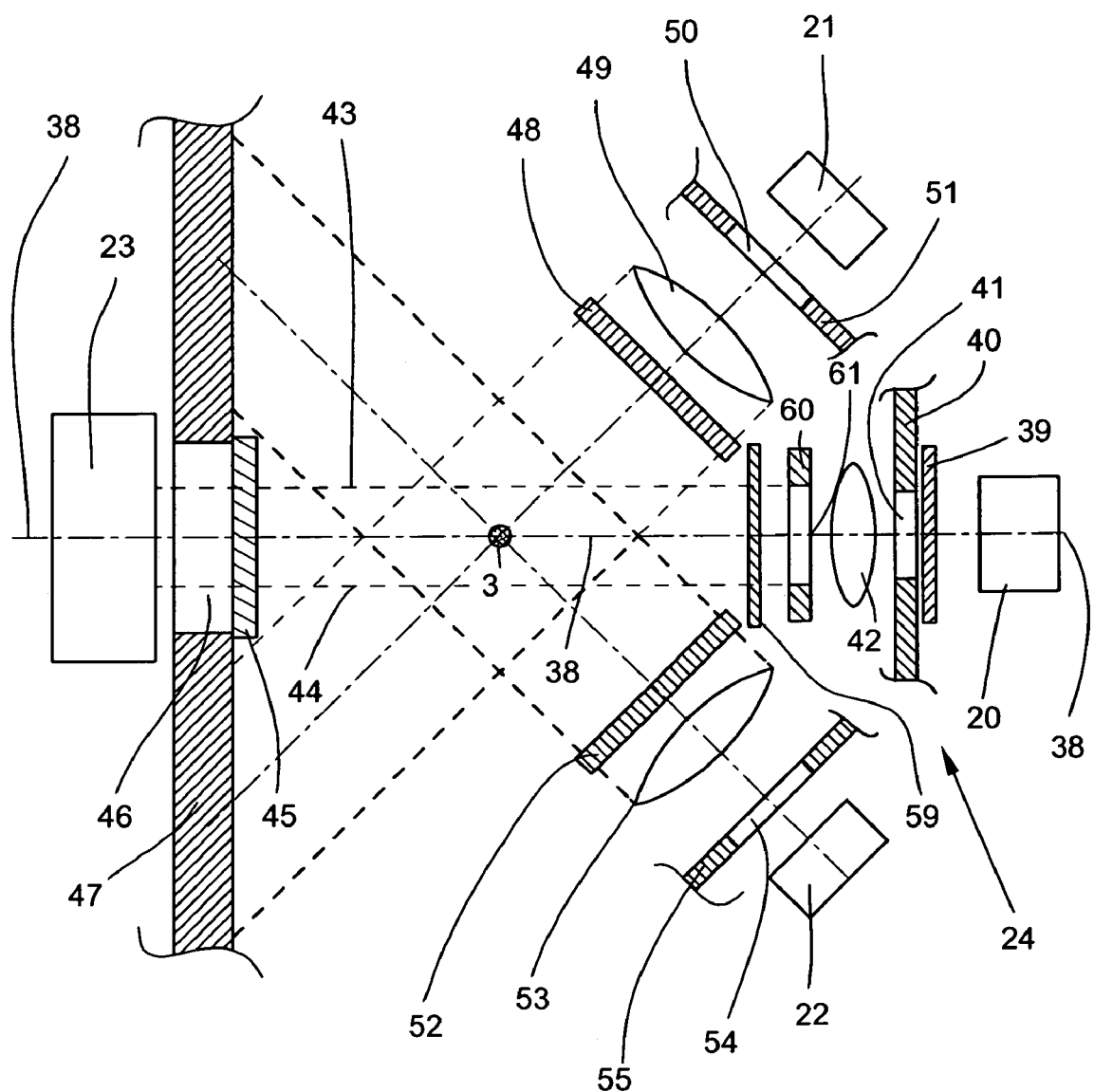
FIG. 3 is an enlarged cross-sectional view of an arrangement of the operative elements of the yarn sensor of FIG. 2.

FIG. 3 shows a more detailed arrangement of the components of the yarn sensor 6, which is suitable for detecting extraneous substances or materials in the yarn 3. As the light source, the light-emitting diode 20 is used, which has approximately the same emission characteristic as a Lambert emitter. The light-emitting diode 20 is embodied as a white-light LED. White-light LEDs emit light with a broademission spectrum. If a white-light LED is used, it is possible to dispense with using a plurality of light-emitting diodes for emitting different colors or for amplifying the emitted light. The light emitted by the light-emitting diode 20 passes through the light transmitting element 24. The element 24 includes a diffuser in the form of a film 39, a diaphragm 40 with an aperture 41, a lens 42, a diaphragm 60 with a rectangular aperture 61, and a glass plate 59, through which light passes in succession in the direction of the optical axis 38. The aperture 41 of the diaphragm 40 has a width of 1 mm. The film 39 projects divergent beams of light and has the emission characteristic of a Lambert emitter. As the film 39, the film type Oracal 8500, translucent series, made by the company known and doing business as K. Gröner is used, for instance. Downstream of the lens 42, the individual beams of light are oriented quasi-parallel to one another in the direction of the optical axis 38 and are distributed homogeneously over the cross section of the total beam of light. The total beam of light is represented by the two dashed lines 43, 44. The film 39 forms a virtual light source, which is projected to infinity.

Along the projected pathway of the beam of light between the lens 42 and the image plane of the photodiode 23, the projection of the virtual light source is always present. This projection itself, however, is blurry. This effect is associated with a further homogenizing of the beam of light. The traveling yarn 3 crosses through the course of the total beam of light and is projected in the form of a shadow on the photodiode 23. Between the yarn 3 and the photodiode 23, the total beam of light passes through both the glass plate 45 and the aperture 46 of the diaphragm 47. Some of the light emitted by the light-emitting diode 20 is reflected by the yarn 3. The photodiodes 21, 22 detect some of the reflected light. Between the yarn 3 and the photodiodes 21, 22, a portion of the reflected light passes through each of the light transmitting elements 25, 26. The reflected light transmitting elements 25, 26 each include the associated glass plate 48, 52, the diaphragm 63, 64, the lens 49, 53, and the aperture 50, 54 of the diaphragm 51, 55, respectively. The reflected light transmitting elements 25, 26 are embodied and disposed such that, if the yarn 3 is absent, then by means of the photodiodes 21, 22 projected images of the opposite surfaces, for instance of the diaphragm 40 or of the wall 62 of the measurement gap 19, are detectable. These surfaces are located on both sides, outside the area of the wall 62 of the measurement gap 19 that is illuminated by the direct radiation of the light-emitting diode 20.

Alternatively, the diaphragms 51 and 55 may be omitted. The glass plates 48, 52, 59 may, in a further alternative embodiment, be embodied as diaphragms and have rectangular apertures.

Figure 4:
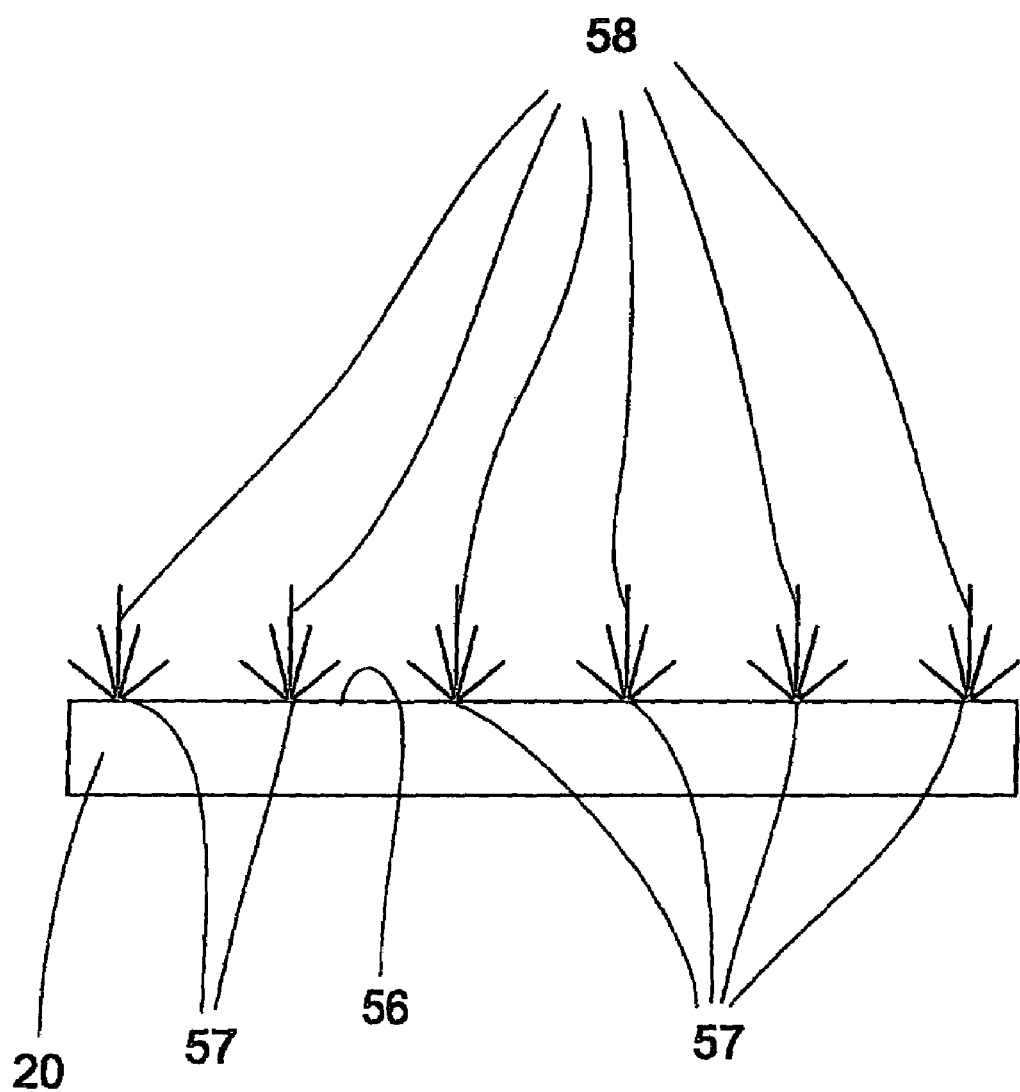
FIG. 4 is schematic illustration of a Lambert area emitter.

FIG. 4 shows the basic illustration of the light-emitting diode 20, whose light-projecting face 56 has the characteristic of a Lambert emitter. From each point 57 of the face 56, a divergent beam 58 is emitted. The light that a Lambert emitter emits can be converted into a homogeneous light with a quasi-parallel beam path; the homogeneity and the parallelism of the light are better than is the case when conventional so-called point light sources are employed.

The invention is not limited to the exemplary embodiments described. Other embodiments are possible within the scope of the invention, in particular as regards the design of the rotor insert. It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

What is claimed is:

1. A yarn sensor for optically scanning a yarn traveling in its lengthwise direction through a measurement gap, comprising:
    a light source for projecting a beam of light across the measurement gap, the light source comprising an emitter having an emission characteristic approaching a characteristic of a Lambert emitter, at least one receiver for directly transmitted light, elements for transmitting the light between the light source, measurement gap and the at least one receiver, comprising:

a first light transmitting element disposed between the light source and the measurement gap and including a diaphragm and a lens, downstream of the light source in the direction of light projection, and arranged such that the diaphragm is projected at least approximately into infinity, and a diffusor disposed between the light source and the diaphragm, the diffusor being adapted to shape the light beam passing through the diaphragm symmetrically to the optical axis of the lens.

2. The yarn sensor of claim 1, wherein the light source is a light-emitting diode.

3. The yarn sensor of claim 2, wherein the light-emitting diode is a white light LED.

4. The yarn sensor of claim 1, wherein the diffusor is a film for generating a divergent beam of light having the characteristic of light emitted by a Lambert emitter.

5. The yarn sensor of claim 1, wherein the lens of the first light transmitting element comprises a light entrance side arranged to homogeneously distribute the luminous intensity the light beam from the light source in the direction of the optical axis of the lens and comprises an exit side arranged to project the light beam arriving from the entrance side essentially parallel to the optical axis of the lens.

6. The yarn sensor of claim 1, wherein the yarn sensor includes second and third receivers for light reflected by the yarn for detecting extraneous fibers.

7. The yarn sensor of claim 6, wherein the light-transmitting elements comprise second and third light-transmitting elements respectively disposed between the measurement gap and the second and third reflected light receivers, each of the second and third light-transmitting elements comprising a lens disposed in the projected direction of the light reflected from the yarn upstream of the second and third reflected light receivers such that, in the absence of the yarn, projected images on an opposing surface of the measurement gap are detectable by the second and third receivers essentially outside both opposite sides of a projected image of the light source across the measurement gap.

8. The yarn sensor of claim 1, wherein the diaphragm between the light source and the lens has an aperture of a width between about 0.8 mm and about 1.2 mm.

9. The yarn sensor of claim 1, wherein a second diaphragm with a rectangular aperture is disposed between the lens of the first light transmitting element and the yarn.

* * * * *